United States Patent
Romman et al.

(10) Patent No.: US 11,875,431 B2
(45) Date of Patent: Jan. 16, 2024

(54) METHOD FOR PROVIDING AUTOMATIC ADAPTIVE ENERGY SETTING FOR CT VIRTUAL MOMOCHROMATIC IMAGING

(71) Applicant: KONINKLIJKE PHILIPS N.V., Eindhoven (NL)

(72) Inventors: Zimam Romman, Jerusalem (IL); Shlomo Gotman, Haifa (IL)

(73) Assignee: KONINKLIJKE PHILIPS N.V., Eidnhoven (NL)

( * ) Notice: Subject to any disclaimer, the term of this patent is extended or adjusted under 35 U.S.C. 154(b) by 496 days.

(21) Appl. No.: 17/263,919

(22) PCT Filed: Jul. 23, 2019

(86) PCT No.: PCT/EP2019/069853
§ 371 (c)(1),
(2) Date: Jan. 28, 2021

(87) PCT Pub. No.: WO2020/025403
PCT Pub. Date: Feb. 6, 2020

(65) Prior Publication Data
US 2021/0304458 A1    Sep. 30, 2021

(30) Foreign Application Priority Data
Aug. 1, 2018   (EP) ..................... 18186810

(51) Int. Cl.
*G06T 11/00*    (2006.01)
*A61B 6/00*     (2006.01)
*G06T 7/00*     (2017.01)

(52) U.S. Cl.
CPC ............ *G06T 11/005* (2013.01); *A61B 6/461* (2013.01); *A61B 6/467* (2013.01); *A61B 6/482* (2013.01);
(Continued)

(58) Field of Classification Search
CPC . G06T 11/005; G06T 7/0012; G06T 2200/24; G06T 2207/10081;
(Continued)

(56) References Cited

U.S. PATENT DOCUMENTS 11,058,384 B2    7/2021   Konno
2003/0042423 A1  3/2003   Bertelsen
(Continued)

FOREIGN PATENT DOCUMENTS

AU    2010237049 A1 * 12/2011  ............. A61B 6/022
EP    3316214 A1      5/2018
(Continued)

OTHER PUBLICATIONS

PCT International Search Report, International application No. PCT/EP2019/069853, dated Sep. 18, 2019.
(Continued)

*Primary Examiner* — Jose L Couso
(74) *Attorney, Agent, or Firm* — Larry Liberchuk

(57) ABSTRACT

An image processing system (IPS), comprising: an input interface (IN) for receiving a request to visualize image data captured of an anatomy of interest by an imaging apparatus (IA). An energy value determiner (EVD) is configured to determine based on at least one of the image data, the different image data or contextual data, an energy value for forming, from the image data, a monochromatic image. The determining by the energy value determiner (EVD) is based on an energy curve fitted to the image data. the image data forms part of a series of sectional images acquired of the anatomy of interest, or such sectional images derivable from the image data. The sectional images relate to different locations (z) of the anatomy. The energy curve is fitted to energy value control points assigned to at least a sub-set of the different locations (z). Each energy value control point
(Continued)

represents a respective known energy value for a respective one of the sub-set of different locations. The system allows efficiently and automatically computing an energy value for any location (z).

10 Claims, 5 Drawing Sheets

(52) U.S. Cl.
CPC .............. *A61B 6/501* (2013.01); *A61B 6/508* (2013.01); *G06T 7/0012* (2013.01); *G06T 2200/24* (2013.01); *G06T 2207/10081* (2013.01); *G06T 2207/30016* (2013.01)

(58) Field of Classification Search
CPC . G06T 2207/30016; G06T 2207/10152; G06T 5/009; G06T 2207/20021; G06T 2207/10072; G06T 2207/30004; G06T 5/50; G06T 11/08; A61B 6/461; A61B 6/467; A61B 6/482; A61B 6/501; A61B 6/508; A61B 6/032; A61B 6/5217; A61B 6/4035; A61B 6/481; A61B 6/505; A61B 6/5205; A61B 6/5258; Y10S 378/901
See application file for complete search history.

(56) References Cited

U.S. PATENT DOCUMENTS

| | | |
|---|---|---|
| 2010/0131885 A1 | 5/2010 | Licato |
| 2010/0310036 A1 | 12/2010 | Burleton |
| 2012/0114206 A1 | 5/2012 | Avinash |
| 2013/0053689 A1* | 2/2013 | Das .......................... A61B 6/03 600/425 |
| 2014/0050378 A1* | 2/2014 | Sengupta ............. G01N 23/046 382/131 |
| 2014/0307847 A1* | 10/2014 | Schmidt ................. A61B 6/032 378/5 |
| 2016/0166221 A1* | 6/2016 | Gao ....................... A61B 6/032 378/5 |
| 2016/0275709 A1 | 9/2016 | Gotman |
| 2017/0069085 A1 | 3/2017 | Sakamoto |
| 2017/0186195 A1* | 6/2017 | Lin ........................ A61B 6/482 |
| 2019/0175130 A1* | 6/2019 | Raman ................. A61B 6/5205 |
| 2021/0267563 A1* | 9/2021 | Sattarivand ........... A61B 6/482 |

FOREIGN PATENT DOCUMENTS

| | | |
|---|---|---|
| WO | WO2016035048 A1 | 3/2016 |
| WO | WO2017013514 A1 | 1/2017 |

OTHER PUBLICATIONS

Pomerantz S. R. et al., "Virtual Monochromatic Reconstruction of Dual-Energy Unenhanced Head CT at 65-75 keV Maximizes Image Quality Compared with Conventional Polychromatic CT1", Technical Developments, Radiology, vol. 266. No. 1, pp. 318-325, Jan. 2013.

Neuhaus V. et al., "Improvement of Image Quality in Unenhanced Dual-Layer CT of the Head Using Virtual Monoenergetic Images Compared with Polyenergetic Single-Energy CT", Investigative Radiology•voo. 00, No. 00, pp. 1-7, 2017.

Wang W.D. et al., "Qualitative Comparison of Noncontrast Head Dual-Energy Computed Tomography Using Rapid Voltage Switching", Journal of Computer Assisted Tomography, vol. 40, No. 2, pp. 320-325, Mar./Apr. 2016.

Neuhaus V. et al., "Comparison of Virtual Monoenergetic and Polyenergetic Images Reconstructed from Dual-Layer Detector CT Angiography of the Head and Neck", Computed Tomography, European Society of Radiology vol. 28, issue 3, pp. 1102-1110, 2017.

Doerner J. et al., "Poly-Energetic and Virtual Mono-Energetic Images from a Novel Dual-Layer Spectral Detector CT: Optimization of Window Settings is Crucial to Improve Subjective Image Quality in Abdominal CT Angiographies", Abdominal Radiology, vol. 43, issue 3, pp. 742-750, 2018.

Alvarez R. et al., "A Comparison of Noise and Dose in Conventional and Energy Selective Computed Tomography", IEEE Transactions on Nuclear Science, vol. NS-26, No. 2, Apr. 1979.

* cited by examiner

METHOD FOR PROVIDING AUTOMATIC ADAPTIVE ENERGY SETTING FOR CT VIRTUAL MOMOCHROMATIC IMAGING

FIELD OF THE INVENTION

The invention relates to an image processing system, to an image processing method, to an imaging apparatus, to a computer program element and to a computer readable medium.

BACKGROUND OF THE INVENTION

In medical multi-energy CT (Computed Tomography) imaging, such as dual-energy CT, provides additional diagnostic capabilities beyond standard energy integrating CT imaging.

One particularly useful type of imagery generatable by multi-energy CT imaging scanners is virtually energy-independent (mono-energetic or monochromatic) images. By applying different energy (keV) settings to generate such images, one can achieve a number of benefits over standard energy integrating CT. For instance, relatively high energy value images (above 70 keV) are less prone to beam hardening artifacts. On the other hand, relatively low energy value images (those below 70 keV) may provide improved low contrast structures resolution and visualization. This may be useful in brain imaging, to better differentiate between grey and white brain matter. Also, using relatively low energy value images may improve visualization of for instance iodine contrast agents administered to the patient before or during imaging.

In current radiology diagnostic reading practice of multi-energy CT, when looking at monochromatic images for a series of images, users (e.g., radiologists) either review multiple image datasets (each with specific keV-setting) or manually change the keV-setting if working at a dedicated dual-energy workstation.

Those routines are either increasing image dataset generation or have negative impact on diagnostic routing workflow.

SUMMARY OF THE INVENTION

There may therefore be a need to improve processing of radiological imagery.

The object of the present invention is solved by the subject matter of the independent claims where further embodiments are incorporated in the dependent claims. It should be noted that the following described aspect of the invention equally applies to the image processing method, the image processing system, to the computer program element and to the computer readable medium.

According to a first aspect of the invention there is provided an image processing system, comprising:

an input interface for receiving a request to visualize image data captured of an anatomy of interest by an imaging apparatus; and an energy value determiner configured to determine based on at least one of the image data, different image data or contextual data, an energy value for forming from the image data a monochromatic image, wherein the determining by the energy value determiner is based on an energy curve fitted to the image data; wherein the image data forms part of a series of sectional images acquired of the anatomy of interest, or such sectional images derivable from the image data, the sectional images relating to different locations ($z$) of the anatomy, the energy curve fitted to energy value control points assigned to at least a sub-set of the different locations ($z$), each energy value control point representing a respective known energy value for a respective one of the sub-set of different locations.

The different image data may stem from a different imaging modality. The different image data may be registered to the image data. The contextual data may describe the image data. The contextual data may be queried from the imaging protocol used by the imaging apparatus when capturing the image data. The contextual image data may be queried by a suitable query interface from medical records, databases or from header files associated with the image data. The contextual data may be supplied by a user of the system (such as a radiologist) through a suitable user interface.

In embodiments, the image processing system comprises an image synthesizer configured to form the monochromatic image based on the determined energy value and the image data. Any desired monochromatic image for any given energy value (preferably specifiable in keV) may be combined from at least two base images acquired in particular in the context of dual energy or photon counting imaging.

In embodiments, the image processing system comprises a visualizer configured to effect the visualization of the monochromatic image on a display device.

The determining by the energy value determiner is based on an energy curve fitted to the image data. Using such as curve, allows for high responsiveness to quickly return the adapted energy setting for display.

Preferably the energy value control points are only assigned to a true subset (in embodiments, to as little as two or three) of the different locations of the image data. The series of section images (also referred to herein as slices) may together form a 3D image volume that includes a representation, in terms or voxel values, of the anatomy of interest. The slice may relate to different axial orientations such as obtainable from known reformatting techniques. The curve can then be used to efficiently and quickly compute a corresponding energy value for any location (in particular other than those to which the (known) energy value control points have been assigned to) based on which a monochromatic image can be formed for the said location. The energy value control points may be formed by a priori known keV values recommend for viewing certain tissue types of combinations. These may be obtained from medical knowledge bases, medical reference works or other sources of medical knowledge.

In embodiments, the image processing system comprises a tissue type determiner configured to determine one or more respective tissue types as represented by respective ones of the sectional images or as derivable from the or other contextual data, and wherein energy value control points correspond to respective one or more of the determined tissue types.

The tissue type determination may include image processing techniques such as morphological image processing and/or segmentation and other. Image values may be compared to known values characteristic to tissue types, such as bone, grey or white matter, fat, muscle or any other tissue type of interest. As mentioned, before the (or different) contextual data may include information encoded in image protocol data structure or meta data such as data header files such as DICOM or other.

In embodiments, the curve is a continuous curve, such as sigmoid type curve.

In embodiments, the anatomy of interest is a human or animal head.

In embodiments, the system comprises a user interface configured to allow a user to adjust the determined energy value. This allows a user to override a value computed by the system.

In embodiments, the image data includes spectral information or such data is derivable therefrom, the image data obtained by dual energy or spectral imaging.

According to another aspect there is provided an imaging apparatus for supplying the image data and the apparatus including the system as per any one of the previous embodiments.

According to another aspect there is provided a method of image processing, comprising the steps of:

receiving request to visualize image data captured of an anatomy of interest by an imaging apparatus; and determining based on at least one of the image data, different image data or contextual data, an energy value for forming from the image data a monochromatic image.

The method comprises forming the monochromatic image based on the determined energy value and the image data. The determining of the energy value is based on an energy curve fitted to the image data. The image data forms part of a series of sectional images acquired of the anatomy of interest, or such sectional images derivable from the image data, the sectional images relating to different locations (z) of the anatomy, the energy curve fitted to energy value control points assigned to at least a sub-set of the different locations (z), each energy value control point representing a respective known energy value for a respective one of the sub-set of different locations.

In embodiments, the image data is in the image domain or in the projection domain. In the latter case, section images in the image domain may be derivable from the projection data by a suitable reconstruction algorithm.

According to another aspect there is provided a computer program element, which, when being executed by at least one processing unit, is adapted to cause the processing unit to perform the method.

According to another aspect there is provided a computer readable medium having stored thereon the program element.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
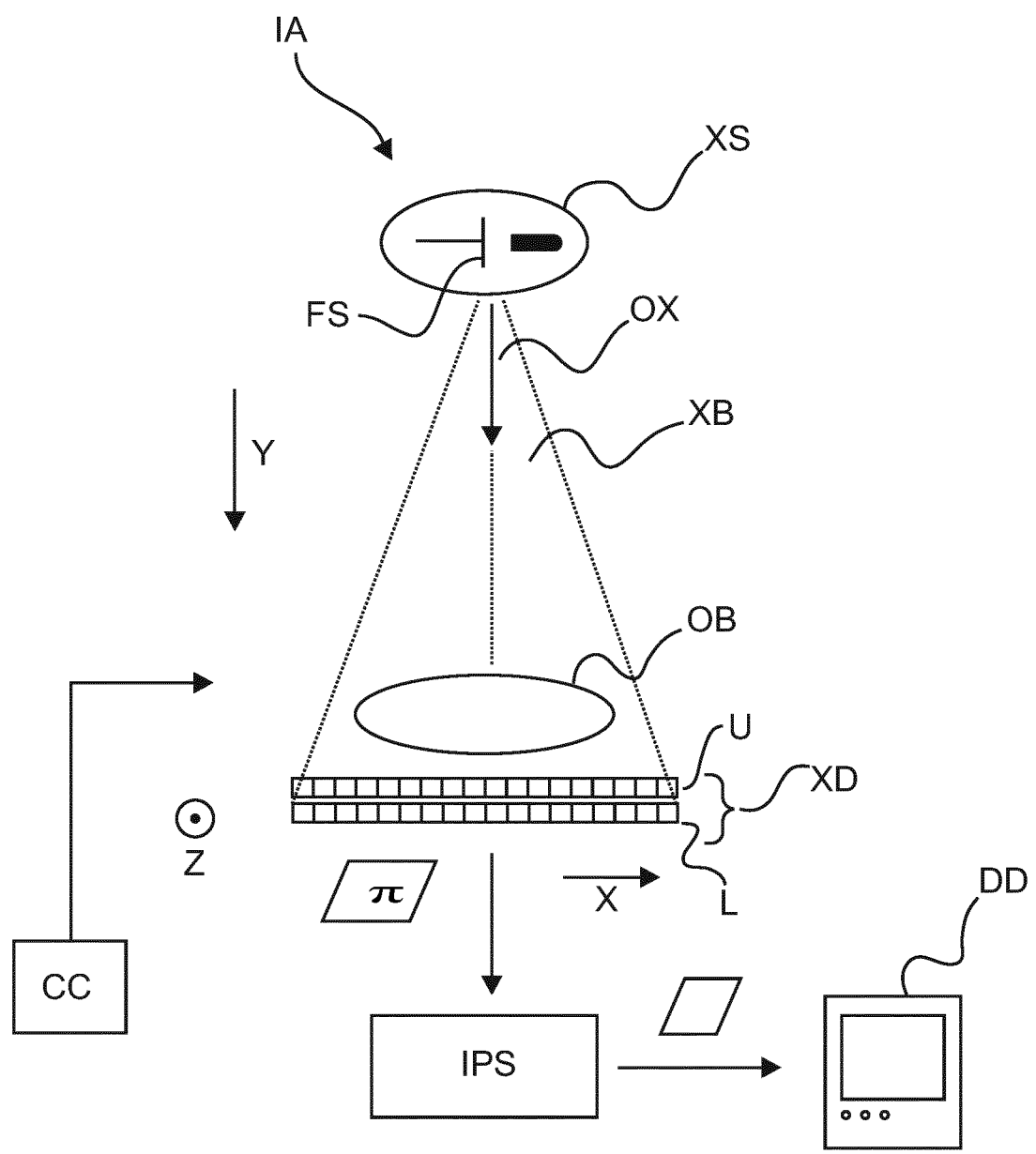
FIG. 1 is a schematic block diagram of an X-ray imaging arrangement.

With reference to FIG. 1, this is a schematic diagram of an X-ray imaging arrangement comprising an X-ray imaging apparatus IA and an image processing system IPS.

The imaging processing system is configured to process image data IM provided by imaging apparatus IA as will be explained in more detail further below.

Turning first to the imaging apparatus IA, this is shown in schematic side elevation view in FIG. 1. Embodiments of the imaging apparatus IA include those configured for volumetric (that is, 3D) imaging such as a C-arm imaging apparatus, a CBCT (Cone Beam CT) scanner, a CT scanner, or a mammography apparatus configured for tomosynthesis or quasi-3D. Alternatively, embodiments configured for (planar) 2D radiography are also envisaged herein. In the following, main reference will be made to CT embodiments, but, again, this is merely exemplary and in no way limiting.

Preferably still, the imaging apparatus IA is configured for spectral or dual energy imaging. In other words, the image data produced by the imaging apparatus IA includes spectral data, on which more further below.

With continued reference to FIG. 1, the imagable object OB is shown in cross-section with an imaging axis Z. In FIG. 1, the imaging axis Z extends into the drawing plane. Although main applications for the X-ray imager envisaged herein are in the medical field, non-medical contexts such as non-destructive material testing or baggage screening, etc. are not excluded herein. Accordingly, the term "object OB" is used herein in the general sense to include animate "objects" such as a human or animal patient, or anatomic parts thereof but also includes inanimate objects.

In more detail, the X-ray imaging apparatus IA includes one or more X-ray sources XS and an X-ray sensitive detector XD. In use, the object OB is positioned along axis Z in an examination region within the X-ray source XS and the X-ray detector XD. The examination region forms a portion of 3D space which is also referred to herein as the image domain. If the object OB is a human patient, a longitudinal axis thereof extends along the Z axis in the image domain. A contrast agent may be administered before or during imaging for better soft tissue resolution. Contrast agent types envisaged may include Iodine, Barium, etc. or admixtures thereof.

The X-ray source XS is energized to produce an X-ray beam XB which emanates from a focal spot FS of the source(s) XS and traverses the examination region and hence at least a region of interest of the object OB. In FIG. 1, OX is the optical axis, and the main propagation direction of the X-ray beam XB, with axis Y parallel to OX. Specifically, the optical axis OX runs from the focal spot FS to detector XD and intersects the detector D at a point. The image plane of the detector XD has coordinates x,z, with axis X being orthogonal to imaging axis Z, and both, axis X,Z, being orthogonal to the optical axis OX or axis Y.

The X-radiation interacts with matter (e.g., tissue, bones, etc.) of the object OB. After interaction, the X-radiation emerges at the far side of object OB to then impinge on the X-ray detector XD. The impinging X-radiation is detected by the detector XD and converted into electrical signals. The electrical signals are converted by suitable analogue-digital AD conversion circuitry (not shown) into projection data it which may then be processed into X-ray images by the image processor IPS as will be explained in more detail below. The X-ray images are capable of revealing details of the internals of the imaged object OB. This can help in diagnosis and therapy or other examination of the imaged object OB. A visualizer VIZ maps image values of the X-ray image to color or grey values. The color or grey values may then be processed by video circuitry that drives one or more display devices DD to so effect displaying of the X-ray images on the one or more display device DD. The appearance of the displayed image may be adjusted, for instance by the user, or automatically, through window/level settings. These settings may be adjusted by suitable user interface(s).

The window/level settings prescribe the manner in which the image values are mapped into interval(s) of grey or color values.

The X-ray images may be stored in a PACS (picture archiving and communication system) of a HIS (hospital information system) or other memory or database or be otherwise further processed.

Turning now in more detail to the processing of the projection data, in embodiments the signal processing chain of the imaging arrangement IA may include a reconstructor RECON that runs a re-construction algorithm such as filtered back-projection, iterative, algebraic or other reconstruction algorithms. Based on the algorithm, the reconstructor RECON converts the projection data $\pi$, which is located in the image plane of the detector XD, into one or more slice images that are located respective planes (in the image domain) perpendicular to the detector's image plane. The re-constructor hence maps the projection imagery $\pi$ from the projection domain into slice imagery in the image domain. It will be understood that in general multiple projection images are acquired, for each imaging position on the imaging axis Z, from different directions of the objects and the reconstructor RECON produces a respective slice image for each imaging position along the imaging axis Z. In CT, acquisitions from different directions is achieved by a rotational arrangement where the X-ray source and/or the detector rotates around the object OB to acquire this set of multiple projection imagery 7E along different directions. During the rotation or in between rotations, there is relative transversal motion along axis Z between the object and the source and/or X-ray detector. In one CT-like embodiment, the transversal motion is effected by advancing an examination table (on which in the patient OB resides) along axis Z during imaging.

The slice images for all covered imaging positions along the imaging axis Z form a 3D image volume V of the anatomy of interest. The anatomy of interest may be a patient's head, chest, heart etc. The spatial coverage (or length) of the volume is preferably commensurate with the longitudinal extent of the anatomy of interest.

In CT or similar volumetric imaging modalities, the image values in each slice image correspond to different locations in the image domain. Each location may be referred to as a voxel coordinate. A voxel coordinate designates both, an image value and a position in 3D in the examination region to which that image value is assigned. Each image is a slice image located in plane X, Y at a particular imagining location z along the axis. Each slice image is hence associated with a unique imaging location z. Each voxel hence comprises a z coordinate and two coordinates x,y in the given plane at z. When referring to image locations x,y in a particular slice image (at z), the image values at said locations may also be referred to as "pixels". In standard formatting, the plane of the slices in the volume V are perpendicular to the imaging axis Z. However, the slice imagery may be reformatted using a reformatting component (not shown). The reformatting tool may be arranged in software to run a reformatting algorithm to compute, from the standard volume V, new series of slice image perpendicular to a new, user specifiable, axis Z' different from the imaging axis Z. The new axis may be non-parallel to the standard imaging axis Z. In this manner a user may for instance reformat cranial head imagery into transverse imagery, etc.

An operation console CC allows a user to initiate imaging and or set imaging parameters, such as any one or more of the following: scan type, body part, and X-ray source (tube) XR settings such as mA, mAs, kVp, rotation time, collimation setting, pitch, etc.

The X-ray tube comprises an anode and cathode. Electrons generated at the cathode emanate from the cathode and are accelerated towards the anode. The electrons interact with anode material to cause the X-ray radiation. mA, mAs relate to the amperage of the cathode current and activation time whilst kVp relates to the maximum voltage across anode and cathode of the X-ray tube XR. The three settings mA, mAs and kVp determine the energy (keV) of photons in the emanating X-ray beam. These setting may hence be called the keV-settings. "Scan type" can be helical or axial and/or may specify the anatomy to be imaged, such as chest, lung, pulmonary embolism, cardiac, etc. "Pitch" is a parameter in multi-slice spiral CT and is defined as the ratio of table increment over detector collimation.

The detector XD may be a flat panel detector, but curved embodiments are also envisaged herein. The detector XD may be of the direct conversion type or of the indirect conversion type.

As mentioned, the imaging apparatus IA is configured for spectral or dual energy imaging. In one embodiment, this is achieved by having the detector XD configured for dual energy imaging. In some exemplary embodiments of such a dual energy imaging configuration, the detector XD comprises two distinct detector layers, one U on top of the other layer L as schematically indicated in FIG. 1. The two detector layers L,U have different radiation sensitivity profiles, in other words, are sensitive to photons of different energies. One layer, U, is sensitive for low energy (referred to herein as the "low energy") photons whilst the other, for instance the lower layer is sensitive for high energy (referred to herein as the "high energy) photons. The low energy sensitive layer U may be arranged on top of the high energy sensitive one L.

In one embodiment, the detector is of the indirect conversion type and the two detector layers U,L can be realized by using materials of different density. For instance, a low density material may be used for the low energy sensitive portion and a high(er) density material may be used for the high energy sensitive layer L. Specifically, the low energy photon sensitive detector layer U may be made from an Yttrium based garnet material whilst the high energy sensitive detection layer may be made from Gadolinium Oxysulfide GOS or other suitable material. By having the layers U,L arranged one on top of the other, natural and simultaneous registration can be achieved.

The projection data detected by the two layers U,L represents spectral data. From this spectral data, virtual monochromatic images for any energy value E (measured in keV) between the upper and lower energies may be derived computationally by means of an image synthesizer IS. It will be understood that in the dual layer set-up as described above, the spectrum provided by the physical x-ray source XR is in general polychromatic. Nevertheless, the virtual monochromatic images can be arrived at through linear combination with suitable weights as will be explained in more detail below. A monochromatic image for a given energy represents an approximation of an image that may have been obtained had a conceptual monochromatic source at the given energy be used for exposure. The conceptual monochromatic source can be thought of as having a single peak energy spectrum.

Specifically, the respective projection data $\pi$ detected at the respective layer L,U for high/low energies may be reconstructed by the re-constructor RECON into two base slice images. The volume V thus includes two so reconstructed base slice images per position z. The base images may relate either to two different, respective, base materials such as contrast material previously introduced into the patient. Alternatively, the two base images may relate to two different manners of tissue versus radiation interaction, such as Compton Scattering and photoelectric absorption. These two effects together combine to account, at least in parts, to the observed attenuation of the X-ray beam XB as register at the detector XD after interaction of the beam XB with patient tissue. As has been reported by R Alvarez and E Seppi in "*A Comparison of Noise and Dose in Conventional and Energy Selective Computed Tomography*", in *IEEE Transactions on Nuclear Science*, Vol NS-26, No 2, April 1979 [see in particular eqs (1)-(3)], once these two base images are gotten for the specific two energies, the upper and lower, any mono-energetic image for any other energy between the upper and lower energy can be computed through linear combination from the two base images. The weights for the linear combination are obtained by evaluating, for the desired energy, functional expressions of the known energy dependence of Compton Scattering and the photoelectric interaction, such as absorption. The Alvarez approach and related approaches harness the fact that the attenuation coefficient is energy dependent.

It will be understood that the dual energy set-up as described above can also be realized with a traditional single layer detector in which case two different x-ray sources are used, each generating radiation at different energies. As a further variant a single x-ray source may be used that can however be switched to operate at different energy levels. In a further embodiment, a photon counting detector set-up is used that is capable of detecting the total energy spectrum (in form of per pixel energy bin histograms) from which the mono-energetic images can be derived computationally.

Being able to produce (virtual) monochromatic images for any given energy between the upper and lower energy is useful as this allows producing tailored imagery with high image quality ("IQ") for any given tissue type or tissue combination one wishes to image. IQ is in particular quantifiable by single noise ratio, contrast noise ratio ("contrast") and brightness or luminance. Different tissue types or combinations thereof can be represented at different contrasts for different energy levels. More specifically, an energy level/setting that may be optimal for one particular material may be inferior for another material of interest.

The proposed imaging arrangement, does not only allow a user to compute monochromatic imagery at the user selectable energy value E (in keV). The proposed image processor IPS is further configured to automatically choose the energy level for any given image slice at a given imaging position z. More particularly, it is proposed herein to automatically select the optimal keV value for the given image anatomy and intended viewing purpose. This allows better diagnostic reading workflow since this eliminates manual selection of keV settings and multiple generation of image datasets during routine diagnostic reading.

Figure 2:
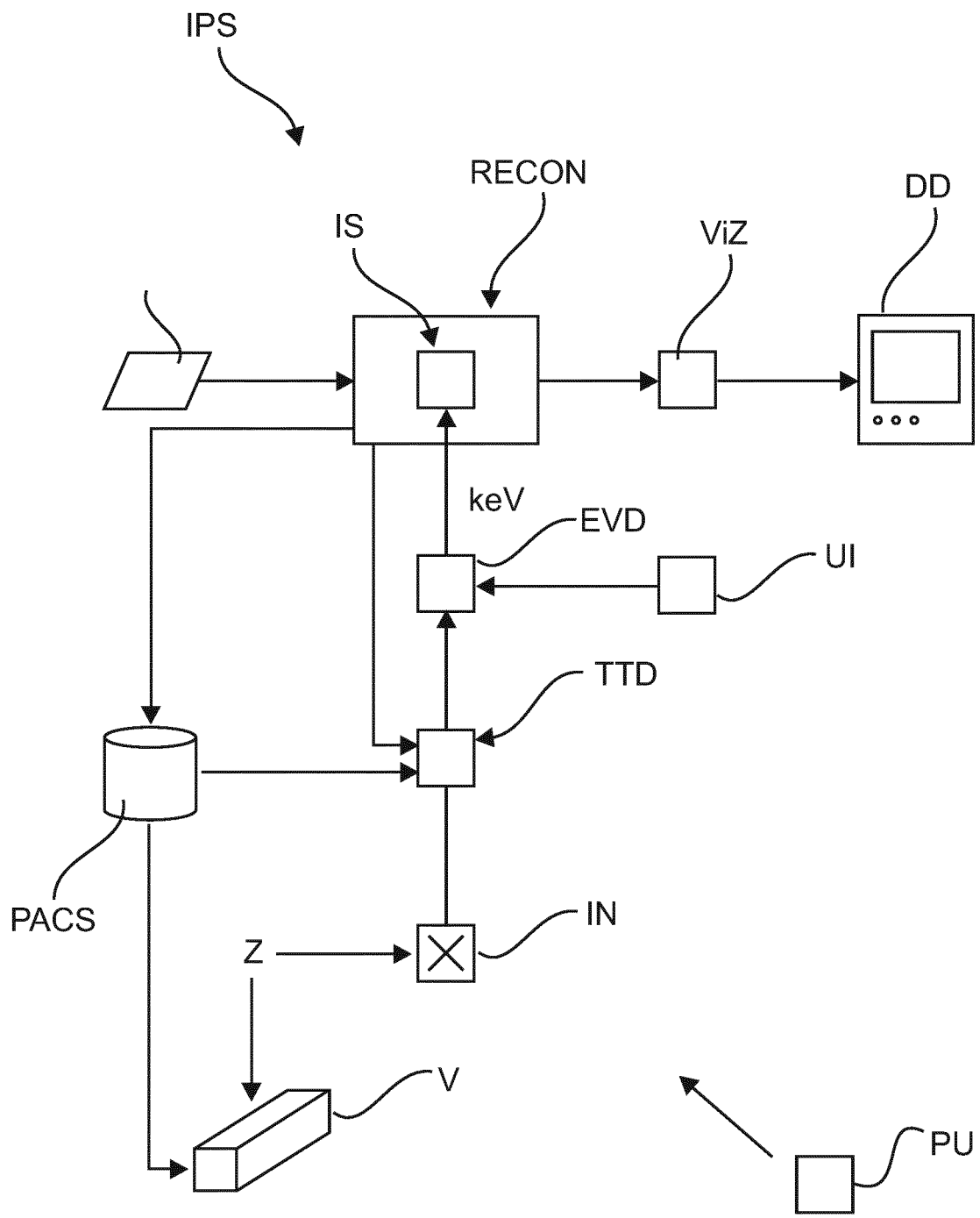
FIG. 2 is a schematic block diagram of an image processing system.

A block diagram of the proposed image processing system IPS for automatic-adaptive energy setting based on anatomy or tissue type as per the imagery at different z positions is shown in FIG. 2. As described, the image processing system IPS may include the re-constructor RECON capable of reconstruction projection π imagery into different slice images (including the two base images) at different z positions. The slice image at different z positions together form an image volume V representing at least a region of interest (ROI) of the imaged object OB. The RECON is optional as the IPS may operate on an existing reconstruction volume V previously reconstructed by the reconstructor RECON in an offline embodiment as will be further explained below.

Broadly, in use, and assuming the volume V has already been reconstructed, a user requests to view a certain slice image at a given position z along the imaging axis Z. The requested position z is received at input port IN. A tissue type determiner TTD then establishes the tissue type or combination of tissue types that is to be expected at the requested position z. The information on tissue type may be derived indirectly from contextual data such as from DICOM metadata in the required projection imagery or the reconstructed image volume V. Alternatively, or preferably, a segmentation or image morphology processing is used by the TTD to examine the previously reconstructed image volume at the requested position z. In one embodiment a conventional slice image is formed at position by adding the two base images that belong to this position. The conventional slice image may be formed by adding the two bases images. For instance, adding of the photoelectric absorption image and the Compton scatter base image allows obtaining a conventional CT slice image which corresponds to a slice image at average energy of the beam XB. Alternatively, either one of the two reconstructed base images at the requested position z of interest may be used for tissue type determination if suitable. If no reconstructed volume exists at the time of receiving the requested position z, survey image data for the purpose of tissue determination may be obtained in a surview or localizer scan. A surview or localizer scan is a planar acquisition with no tube XS rotation, where a low-dose image is acquired at a lower dose than during rotational acquisition. Alternatively, it may be sufficient to segment the projection data 7E to identify tissue type(s). Yet alternatively, previous imagery obtained by a different imaging modality (e.g., MRI or emission imaging modality SPECT, PET, etc.) may be used to determine the tissue type at position z. Instead of in addition to image segmentation, morphological image processing is used to determine tissue type(s).

A suitable energy value E corresponding to the determined tissue type or tissue type combinations at position z is then derived by an energy value determiner EVD, the operation of which will be explained later more fully below at FIG. 3. The determined energy value is forwarded to the image synthesizer IS to synthesize from the reconstructed base images at position z in volume V, the desired virtual monochromatic image for the automatically determined energy value.

The monochromatic image may then be processed by a visualizer VIZ to produce a visualization of the monochromatic imagery in grey value or color value coding and this is then displayed on the display device DD. The conversion into suitable image values include conversion into any one of Hounsfield units, HU, material concentration MG/CC or affecting atomic number value Z.

The determined energy value may be changed or overridden by the user through a suitable user interface UI. In this case, the image synthesizer IS recomputes the monochromatic image based on the user provided, new energy value.

The energy value determiner EVD may retrieve the energy values for the monochromatic image based on medical reference records that table or detail suitable energy values for view for different tissue types. However, preferably, and as is proposed in a preferred embodiment, an energy curve S is computed based on the specific image volume V. The computation carried out by the energy value determiner EVD may include fitting the curve to preferably only a few (as little as two or three) prescribed energy values (referred to herein as energy control points) for certain sampling positions along Z. The curve S may be fit to any number of energy control points. The energy curve describes a functional relationship between the z positions on the relevant axis Z and the energy value associated with that position and hence with the tissue type composition at the respective energy imaging position z. This is illustrated diagrammatically in FIGS. 3A and B to which reference is now made. The above described embodiments assumed that the volume has already been reconstructed and these embodiments may hence be called off-line embodiments. Real-time or online embodiments are also envisaged, where no or not all slice images that are to form the volume have been reconstructed yet. In this case, once a position is requested, the two base images are reconstructed for this position and for at least one or more positions (such as three or more or all positions z) to be able to reliably fit the energy curve S. The energy value is then determined as described above, and the synthesizer IS then computes the monochromatic image for the determined energy value. The monochromatic image is then displayed for the user.

Figure 3A:
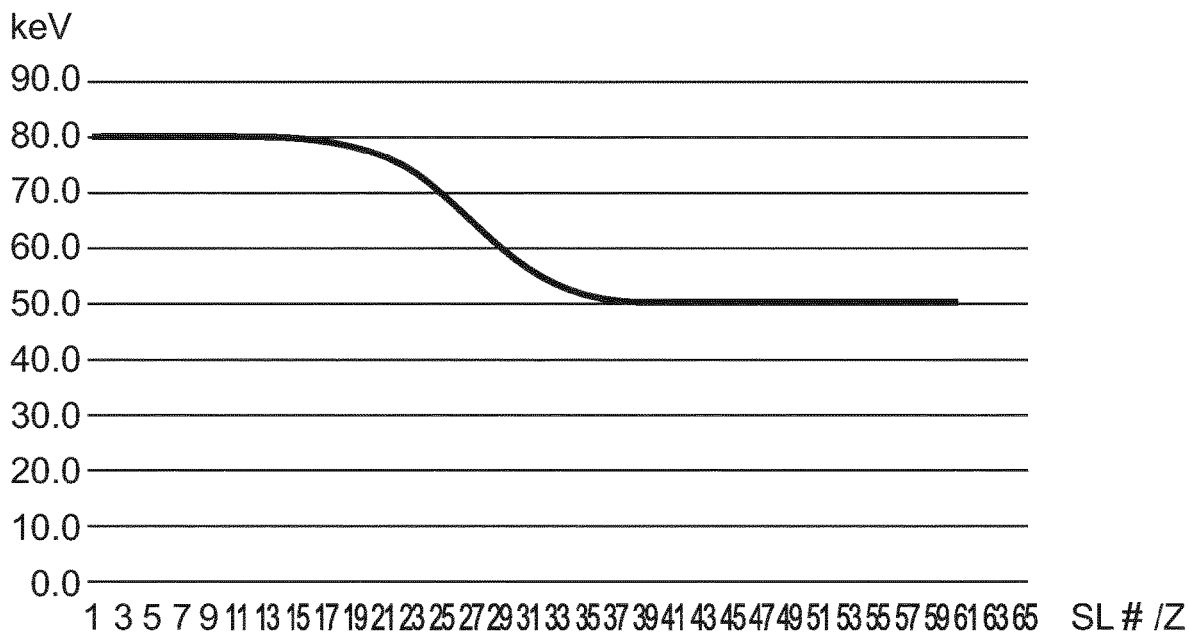
FIGS. 3A,3B illustrate exemplary energy curves fitted to image data.

FIG. 3A shows an example of an energy curve as envisaged herein where energy values are associated with respective z positions (or slice numbers #) in a given volume V. The example in FIG. 3A is drawn from head or skull imaging but is of general application and can be used for other anatomies or even for non-medical context equally. As can be seen, there are two regions of constancy where a value of energy value of 80 keV and 50 keV are respectively assigned. In between the two regions of tissue type constancy there is a transition region where the energy value values transition from one of the prescribed values to the other. The transition region corresponds to regions where there is a mix of tissue types. The transition is preferably gradual and forms in one embodiment a sigmoid curve as shown in FIG. 3A while other function types such as linear, piecewise linear, pricewise linear and constant, non-linear, piecewise non-linear, etc. may be used instead. The function is preferably capable of modelling transitions. Combinations of same or different function types may be used, such as a sum of different sigmoid functions. Types of sigmoid functions envisaged herein include logistic, hyperbolic tangent, arctangent, Gudermannian, and many others. Certain probability distribution or density functions may also be used.

Figure 3B:
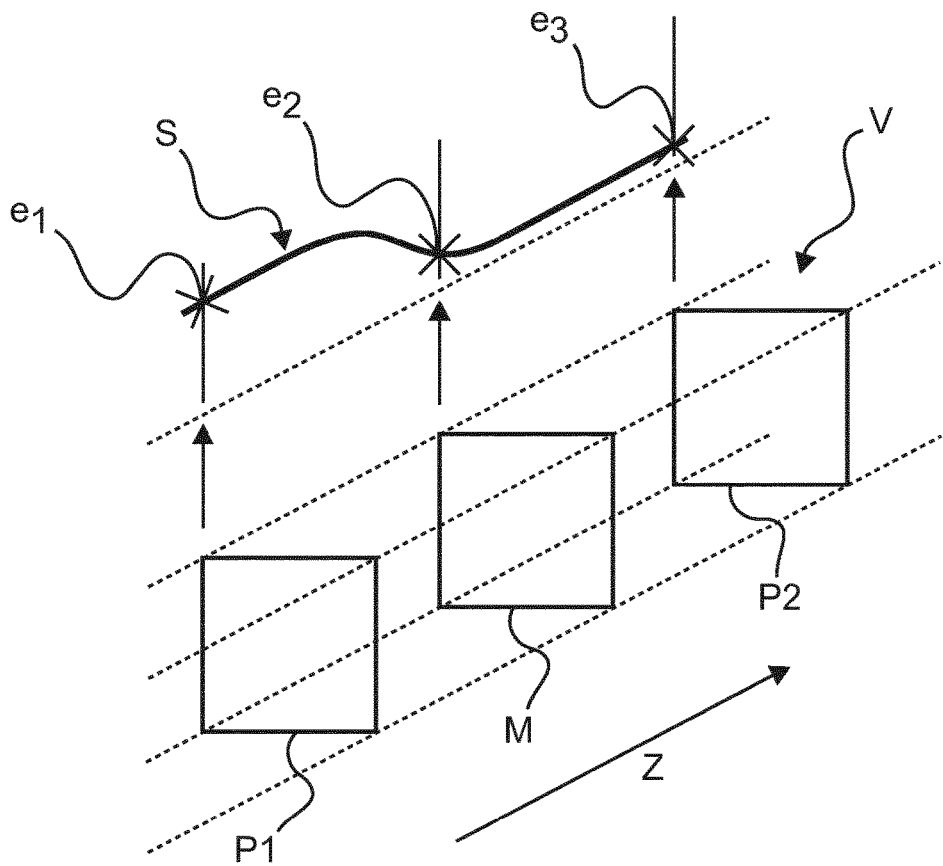

FIG. 3B further illustrates the energy curve S versus z position at the example of three slice images P1, M and P2 at different z positions. Regions of tissue type constancy, such as for imagery P1 and P2, correspond to z positions where a relatively homogeneous tissue composition can be found. In other words, images P1 and P2 form relatively "pure" images that represent respective pure tissues for which the respective energy values e1, e3 are known and have been so assigned. In between the two pure images P1 and P2 may be a mixed image M that represents a mix of tissue types.

As proposed herein, given known energy control points for the pure imagery P1, P2, the, preferably continuous, energy curve S is fit thereto to so define an energy value e2 even for the respective mixed imagery M for which the best energy value may not be easily known. The control points may not necessarily relate to pure images P1, P2 but to any images whose preferable energy values are known and or can be derived.

It is then proposed herein to use the tissue type determiner TTD to determine tissue type or tissue combination of respective images in the volume and to assign to imagery that relates to relatively homogeneous tissue composition an a-priori known energy value that may be referred to herein as energy control points. The remaining mixed imagery in intermediate Z sections is then interpolated based by fitting a curve through the a-priori known values at certain, for instance pure images P1, P2. Preferably and in embodiments, the EVD is configured to also compute a control point energy value for at least one position where a mixed image M is located or at an interface position $z_{IF}$ where an interface image M' is located. Interface image M' is one that represents a location where two different tissue types meet, preferably with noticeable x-ray attenuation. An example for such an interface position is the caudal end of the posterior fossa region in brain imaging. The posterior fossa region is advantageous for brain imaging because it is surrounded by relatively hard and massive bone tissues compared to the rest of the head resulting in noticeable attenuation differences.

The IPS may be integrated into the imaging apparatus IA or may be arranged in a general purpose computing system associated with the imaging apparatus IA. The image processor IPS may be implemented as a software module resident on the work station associated with the imaging apparatus or alternatively, the image processing system IPS may be implemented in a cloud architecture and distributed across one or more computing systems, such as servers, remote from the imaging apparatus IA. In the latter case the projection imagery $\pi$ is forwarded through a wireless or a wired communication network to the one or more computing units PU that implement the image processing system IPS.

Some or all components may be arranged in hardware such as a suitably programmed FPGA (field-programmable-gate-array) or as hardwired IC chip. Specifically, one or more features of the IPS as disclosed herein may be configured or implemented as/with circuitry encoded within a computer-readable medium, and/or combinations thereof. Circuitry may include discrete and/or integrated circuitry, application specific integrated circuitry (ASIC), a system-on-a-chip (SOC), and combinations thereof, a machine, a computer system, a processor and memory, a computer program.

Figure 4:
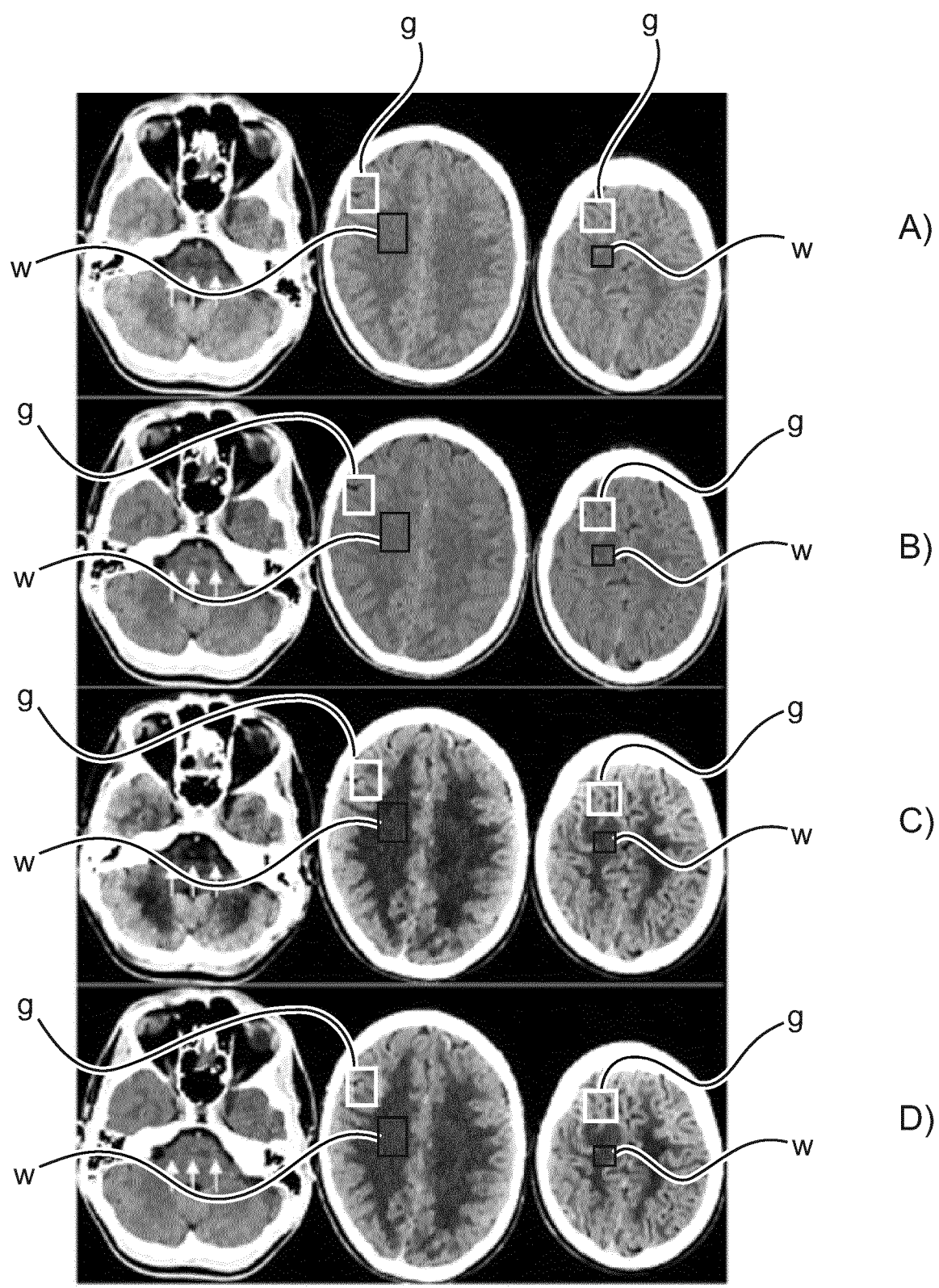
FIG. 4 is exemplary CT X-ray imagery obtainable by the proposed image processing system and method.

Reference is now made to FIG. 4, where exemplary CT brain imagery is shown to illustrate the usefulness of the proposed image processing system IPS. FIG. 4 shows four rows A-D. Each row shows cross-sectional imagery from caudal (left) to cranial position (to the right). All images in each row show unenhanced CT brain images at the same three acquisition locations Z. All images are displayed with the same window level width such as 35/70. As can be seen in the imagery, the visual appearance changes for different energy levels for the same window level/with setting.

The first row A, shows conventional slice images with posterior fossa artifacts as indicated by the arrows. There is moderate grey matter G and white matter W contrast. Rows B and C show different monochromatic images where the same energy value is used for each section. For instance, in row B, an energy value of 90 keV is used throughout whilst row C shows 40 keV monochromatic imagery. While the respective left images show reduced posterior fossa artifacts, contrast in the middle and right images has deteriorated for grey and white matter. If 40 keV monochromatic images are produced for all three sections, then the artifacts in the posterior fossa region deteriorate whilst there is more contrast for grey/white matter as shown in the middle section in row C. However, in row C the grey matter contrast may be characterized as over contrasted whilst the grey/white matter contrast in the right image has improved.

Row D shows advantageous effects of applying the proposed image processing apparatus IPS with adaptive, anatomy-based, different monochromatic energy levels for each section. In the left image, a 90 keV monochromatic image was produce, whilst for the middle and right sections 45 and 40 keV monochromatic images were produced, respectively.

Overall, as evidenced in row D, there is reduced posterior fossa artifacts in the left section and there is enhanced grey/white matter contrast g,w in each of the middle and right images. In other words, by automatically producing optimized monochromatic images for different anatomic sections Z in volume the image quality can be maintained no matter which section is being viewed by a user (such as the radiologist.

Figure 5:
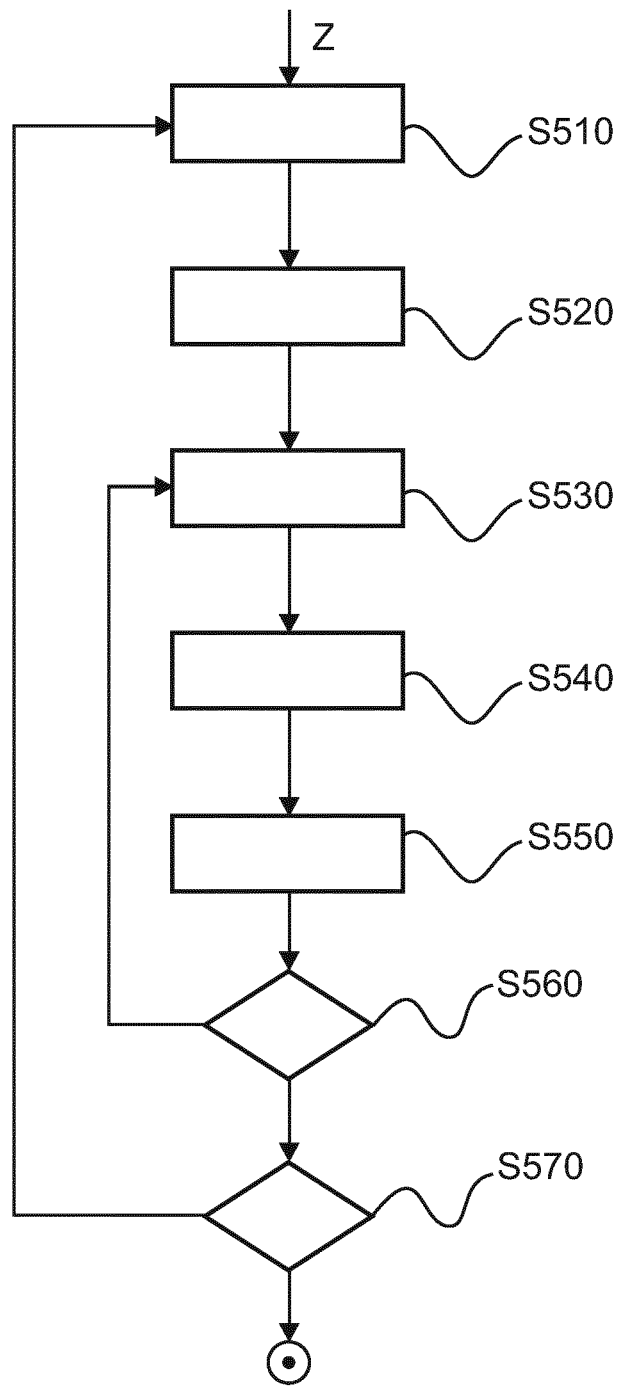
FIG. 5 is a flow chart of an image processing method.

Reference is now made to flow chart in FIG. 5 to describe a method of image processing as implemented by the image processing system IPS. However, it will be understood that the steps described in the following are not necessarily tied to the architecture of the image processing system IPS as described above, but the following steps may also be understood as a teaching in its own right.

Broadly, in the proposed method for image processing, automatic, preferably gradual, change in selection of Key settings for mono-energetic images at different locations within the scanned range is provided. This ensures consistent image quality with respect to the intended usage. The proposed automatic calculation of optimal energy values has been found to be of particular benefit in CT head/brain scans at any acquisition level, although application to other anatomies are also envisaged herein.

The proposed automatic keV adaptation is based on an anatomy or tissue type or on tissue combination. The method is preferably implemented as a functionality that is optional in embodiments. A user interface may be provided that allows the user to enable or disable the functionality. If enabled, the method will preferably automatically execute once the user has specified an image location at which the image data should be visualized.

Initially, at step S510, a request is received (for instance, originating from the user) to visualize image data. The image data may comprise projection data or volumetric data V reconstructed from the projection data. The image data represents an anatomy of interest.

The image data has been preferably acquired by an imaging apparatus capable of spectral of dual energy imaging. The request specifies in particular a position z (or a range of positions) on an image axis Z, at which positions z respective slice images are to be brought up for visualization on a display device.

At step S520, based in part on the image data and/or on contextual data in relation to the image acquisition, an energy value is determined for forming a monochromatic image based on at least part of the image data. The energy value determination may also be based on other image data registrable from the image data. The other image data may have been obtained by a different modality such as MRI or other.

As mentioned, the request at S510 preferably includes the imaging position z. The imaging position may relate to a specific anatomic location which is of interest to the user. More specifically, in the CT embodiment the image position z relates to a specific location on the imaging Z axis and hence to a certain anatomic location and it is image data for the said location z that is to be visualized by means of a monochromatic image.

The imaging apparatus is preferably an X-ray image apparatus and may have a radiation source (e.g., X-ray tube) that is polychromatic. It is the polychromatic x-ray tube that was used to capture the image data. Nevertheless, the monochromatic image represents an approximation for an image obtainable had a monochromatic radiation source been used.

Determination of tissue type, or of a mix of tissue types, at step S520 may be indirectly derived from contextual data such as from information on the scan type used to acquire the image data. Such contextual data may be specified in image protocol data. From this image protocol data or from other contextual data, the anatomical area of interest may be concluded, and hence the tissue type(s). For instance, the scan type may specify that a contrast or non-contrast head scan was performed.

In the alternative, or in addition, an image analytic processing is performed such as a segmentation or an image morphological analysis to determine the tissue type(s). The image processing may be performed on exploratory or surview image data obtained from the patient in a low dose scan. Alternatively, the image processing may be performed on the image data itself, that is, either on projection data or on the reconstructed volume (at the requested imaging position z), if this has already been reconstructed.

Once the anatomy of interest at the requested imaging position z, is identified, and hence the one or more tissue types, a related value Key is determined at step S530 based on the tissue type or tissue type combination.

The determination may be based in addition or instead on medical data records on other image data acquired by a different modality. The different image data may be either natively registered to the image data to be visualized, or the said different image data may need to be registered, rigidly or non-rigidly, to the given image data by using an image registration algorithm.

The energy value to be determined can then be used at step S540 to form, from the image data, a virtual monoenergetic image for the requested location z. The above discussed image synthesis methods of Alvarez or related techniques may be used for the synthesis. Photon-counting based monochromatic image syntheses is specifically envisaged herein in embodiments.

At step S550, the monochromatic image may be mapped to color or grey value encodings or otherwise and is then displayed on a display device DD.

At step S560, an optional request by the user is received to modify the automatically computed energy value at step S530. Process flow then returns to step S530 with a new energy value provided by the user and a new monochromatic image is then re-computed at step S540 based on the newly provided image energy value and then this is displayed at step S550.

Process flow may then proceed to step S570 where it is determined whether automatic generation of a new monochromatic image for a different location z' is requested. If not, then the process flow ends. If yes, the process flow returns to step S510 and is repeated as previously described with the said newly requested image location z'.

The step S530 for determining the (preferably optimal) keV value for a given image location z may be derived from medical reference works. These works prescribe from experience suitable desirable energy values for different anatomies or parts thereof. Preferably, however, and as proposed herein, an energy curve S is fitted to preferably the whole image volume to so assign automatically, for each sectional position z, a suitable energy value. The assigned energy value preferably improves image quality, for each position singly, when brought up for visualization. So rather than using a priori known energy values for each and every sectional image position z, only a sub-set of energy values, referred to here as energy control points, may be used. Only these energy control points may then need to be known. Preferably, but not necessarily, these energy control points are assigned to locations z that are relatively homogenous, that is, locations that relate to a single or very few tissue types or where a certain tissue type is most dominant. At these locations, the optimal energy values may be well understood and readily known. For intermediate locations that may relate to more heterogeneous mix of different tissue types, the energy values for image quality improvement, may then be interpolated from the known energy control points by fitting an energy curve of a pre-determined type, such as a sigmoid type, as explained above at FIG. 3A, B.

In head or brain imaging for instance, the main tissue components involved are bone, grey/white matter and a mix of bone and grey/white matter. The, for IQ purposes, optimal energy values for grey/white matter on the one hand and bone on the other, are understood to be about 50 keV, 80 keV respectively. A suitable energy value may thus be extrapolated from these two energy control points, based on the fitted energy curve, for intermediate locations z between those known locations of relative tissue purity. More specifically, and with particular reference to head imaging, it is proposed herein to automatically identify the location of the (caudal) end of the posterior fossa region and to then assign an appropriate energy value x keV to this location, with "x" being in between two control point energy values, an upper and lower one. An energy curve such as a sigmoid function is then fit to x and the upper and lower control points to so achieve a gradually-changing keV values between the upper and lower control point energy values. Example values for intermediate point is 70 key, and the upper and lower keVs being 80 keV and 50 keV. 80 keV corresponds to the known preferable (or optimal) energy values for bone (in particular the posterior fossa region) whilst 50 keV corresponds to the known preferable (or optimal) value for grey/white brain matter. The intermediate value, in this case 70 keV, may be chosen to a scoring scheme as will be described more fully below. The score measures whether tissue mix at the intermediate position is more like bone or like grey/white matter.

In the following, two embodiments of step S530 will be described with particular reference to brain or head imaging. One of the embodiments is based on morphological image processing or segmentation whilst the other embodiment uses average anatomical measurements to assign an energy value to a particular z position of an anatomy.

Turning now first to the image processing based embodiment of step S530, the following sub-steps, (some of which are optional), are envisaged herein. The following will be explained with particular reference to finding an interface location M' in the context of brain imaging to assign an intermediate value thereto, in between two other energy values, a maximum or a minimum, such as 50 and 80 keV or other. In particular, such a location has been found to be the caudal end of the posterior fossa region. In one embodiment, the intermediate value is 70 keV.

In the said first embodiment, the caudal end of the posterior fossa region is found based on morphological image processing. Broadly, a score value is computed, dependent on position z. The score value quantifies, based on image information in the slice image at z, the contribution of each tissue type, in this case bone or brain matter (grey and white). This may be formulated as a bone fraction to quantify "hollowness": the less bone there is, the hollower the skull section represented in the slice image at a given position z.

In a step 1 of this embodiment, bone segmentation is performed, for instance thresholding to define a skull segmentation. A convex hull or envelope is then created in the slice image at a given position z. The convex hull/envelope encloses the skull segmentation in the slice image. This operation may be topologically conceptualized as a stretching a conceptual rubber band around all image structures. However, this hull is likely to account also for small singularities which are image portions that do not or not necessarily represent skull bone but may have a similar structures and hence may be prone to misclassification. In general, the segmentation decomposes the image into, by convention, "white" and "black" pixels, with white representing bone and black non-bone. Again, this is conventional and an opposite encoding may be used. Also, black/white as used herein is merely a shorthand to distinguish pixel classes and does not necessarily imply that a visualization is intended. Indeed, the described morphological and/or segmentation operations may be performed without any visualization.

In a step 2, these singularities are eliminated. If the slice image would indeed represent a continuous round shape (as one can expect for an ideal skull shape), the outline of this convex hull would have a nearly "perfect fit" around the shape and one would expect a relatively small number of "floating" edges". A floating edge is a subset of pixels that connect regions of white pixels that are separated by a black pixel region.

In order to achieve this singularity elimination, one needs to remove small bone like singularities (such as bone-like image artefacts, bones, etc. . . . ) and readjust the convex hull accordingly. Such singularities can be identified in several ways, all envisaged herein in different embodiment to which we now turn in more detail, although the present disclosure shall not be construed as so limited:

In embodiments, singularities are identified as blobs (of a user definable, preferably relatively small, size) of pixels which are relatively isolated from the rest of the white pixels that represent the skull.

In other embodiments, a propagation approach is used. In this approach, a propagation, at a suitable step length, is performed along an outline of the convex hull and one searches for a (preferably) short-length polygonal chain (also known as a polygonal path or poly-path), preceded and followed by floating edges. This will most likely indicate a singularity which can be removed.

In other words, after removal of one or more singularities, the convex hull is re-computed to readjust the fit, thus making its "tighter" around the skull image object.

In a step 3, a morphological erosion operation is performed. In particular, in the possibly adjusted convex hull that is fit as tightly as possible to the main object of the image, one erodes exterior pixels of the bounded shape, in an attempt to "peel off" the skull, and one remains with objects inside the skull object that possibly represent inner bones. The erosion is done by starting from each pixel individually along the outline of the convex hull, and projecting "erosion rays" inwards in various directions, each such ray terminating, once emptiness, that is, a black pixel region, is reached. The rays thus eliminate anything in their respective paths.

The output at this stage is a processed slice image with skull pixels removed and we remain only with inner bone representing white pixels.

If the current slice image represented a completely hollow skull object (which may be thought of visually as an oval shaped disk), we should remain with very few white pixels, that is pixels that represent inner bones. Specifically, images of the top, sagittal, few slices of the skull can be expected to include a solid white round shape, which would also leave us at this point with no remaining inside white pixels. On the other hand, lower more caudal parts of the skull, will gradually become less hollow due to mouth/nose/jaw bones, etc., emerging and would leave us with increasingly white pixels. So, in order to determine the "hollowness" for each slice image z, we measure the ratio between the area size of remaining white areas and the size of the complete area within the convex hull. This ratio may be taken then as a final score of hollowness for the given image at z.

The final score at each of the z's may then be used to map to keV values. Each score value at position s(z) may uniquely determine a section through a generic skull, including those sections where the keV values are known. The energy curve such as the sigmoid function may be fit through those control points to so define a keV value for all z position. In one embodiment, a sigmoid function may be used, such as:

$$y(s_i) = \text{keV}_{max} - (\text{keV}_{min} - M) * z, \quad (1)$$

wherein:
$s_i$ is the score of the slice #i (counted/measured by convention from the cranial end of the skull),
y is the keV value for slice #i,
$z = 1/1 + e^{-\alpha(s_i+\beta)}$, with M, $\alpha$, $\beta$ optional fitting parameters.

The known energy control points are $\text{KeV}_{max}=80$ (for pure bone) and $\text{KeV}_{min}=50$ (for pure brain matter), but this is example values of the specific embodiment of brain imaging. Other values may be used in other cases.

The above steps for defining the score values and the morphological operations are all exemplary embodiments, and other image processing operations such as segmentations or other based on other than morphology for quantifying and characterizing tissue type mixtures are also envisaged herein. It will be also readily understood, that other score values may be defined to capture the notion of hollowness in other anatomical settings such as pelvis imaging. Also, in other anatomic settings, concepts other than hollowness may be used to find certain locations for assigning energy values thereto. In general, the score value concept as described herein measures the mix of tissue types and the preponderance of one or more of its tissue components, the assumption being that the energy values for one or more or all the tissue types being known in isolation. The score value may not necessarily be scalar but may be vectorial such as $s=(s_1, s_2, \ldots, s_k)$, each $s_k$ representing the preponderance of tissue type k.

In the second embodiment of step S530, the location for the end of the posterior fossa region estimation is based on empirical skull anatomy. This embodiment is based on an assumption that the posterior fossa border for normal adult skull is located about 100 mm from the end of the skull (last CT image with skull contents). The sigmoid function that provides fair approximation for the variable keV may then be written as follows:

$$y(x_i) = \text{keV}_{max} - (\text{keV}_{min} - M) * z, \quad (2)$$

wherein:
$x_i$ is distance in mm of the slice #i (counted/measured by convention from the cranial end of the skull),
y is the keV value for slice #i, $$z = 1/1 + e^{-\alpha(s_i+\beta)}$$

with certain optional constants which can be adjusted for any given use case:

As mentioned above, in exemplary embodiments in brain imaging, with known energy control points of $\text{KeV}_{max}=80$ (for pure bone) and $\text{KeV}_{min}=50$ (for pure brain matter), one may choose optional fitting parameters M=20, $\alpha=0.117$, $\beta=94.6$, but again, these values, although envisaged in embodiments, are primarily included herein as examples for illustration purposes. As can be seen, in energy curve eq (2), the keV are now in terms of distance x rather than in terms of score values s as in the earlier embodiment eq (1). The calculations are to be adjusted for smaller skull size proportionally. The actual skull size can be estimated by standard bone segmentation methods.

The energy value determining step S530 in either of the above embodiments based on the energy curve S may be done in a pre-computation phase offline, and may also be done on demand online when the user requests visualization of the respective slice images at a given imaging position z. To enhance the responsiveness of the system however a pre-computation is preferred in embodiments.

Although in the above explained step of the method main reference was made to processing in image domain, all or parts of the steps may be practiced in projection domain.

Furthermore, although the above steps have been explained with main reference to positions z on the standard imaging axis Z, the above is of equal application for other axis z' obtainable by reformatting and this is envisaged herein in embodiments.

The above method is also applicable to a series of radiographs.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
   an imaging apparatus configured to capture image data of an anatomy of interest;
   an input interface configured to receive a request to visualize the image data; and
   an energy value determiner configured to determine, based on at least one of the image data, different image data or contextual data, an energy value for forming, from the image data, a monochromatic image; wherein the determining by the energy value determiner is based on an energy curve fitted to the image data; wherein the image data forms part of a series of sectional images acquired of the anatomy of interest, or such sectional images derivable from the image data, the sectional images relating to different imaging locations along an imaging axis of the anatomy, the energy curve fitted to energy value control points assigned to at least a sub-set of the different imaging locations, each energy value control point representing a respective known energy value for a respective one of the sub-set of different imaging locations.

2. The image processing system according to claim 1, comprising an image synthesizer configured to form, from the image data, the monochromatic image based on the determined energy value.

3. The image processing system according to claim 1, comprising a visualizer configured to effect the visualization of the monochromatic image on a display device.

4. The image processing system according to claim 1, comprising a tissue type determiner configured to determine one or more respective tissue types as represented by respective ones of the sectional images, and wherein energy value control points correspond to respective one or more of the determined tissue types.

5. The image processing system according to claim 4, wherein the curve includes a sigmoid type curve.

6. The image processing system according to claim 1, wherein the anatomy of interest includes a head of a human patient or a head of an animal patient.

7. The image processing system according to claim 1, comprising a user interface configured to allow the determined energy value to be adjusted.

8. The image processing system according to claim 1, wherein the image data includes spectral information, the image data obtained by dual energy or spectral imaging.

9. A method for image processing, comprising:
   capturing image data of an anatomy of interest;
   receiving a request to visualize the image data;
   determining based on at least the image data, different image data or on contextual data, an energy value for forming from the image data a monochromatic image; and
   forming the monochromatic image based on the determined energy value and the image data, wherein the determining of energy value is based on an energy curve fitted to the image data; wherein the image data forms part of a series of sectional images acquired of the anatomy of interest, or such sectional images derivable from the image data, the sectional images relating to different imaging locations along an imaging axis of the anatomy, the energy curve fitted to energy value control points assigned to at least a sub-set of the different imaging locations, each energy value control point representing a respective known energy value for a respective one of the sub-set of different imaging locations.

10. A non-transitory computer-readable medium for storing executable instructions, which when executed by at least one processor, cause the at least one processor to perform a method for image processing, the method comprising:
   capturing image data of an anatomy of interest;
   receiving a request to visualize the image data;
   determining based on at least the image data, different image data or on contextual data, an energy value for forming from the image data a monochromatic image; and
   forming the monochromatic image based on the determined energy value and the image data, wherein the determining of energy value is based on an energy curve fitted to the image data; wherein the image data forms part of a series of sectional images acquired of the anatomy of interest, or such sectional images derivable from the image data, the sectional images relating to different imaging locations along an imaging axis of the anatomy, the energy curve fitted to energy value control points assigned to at least a sub-set of the different imaging locations, each energy value control point representing a respective known energy value for a respective one of the sub-set of different imaging locations.

\* \* \* \* \*